(12) United States Patent
De Wit et al.

(10) Patent No.: US 10,416,567 B2
(45) Date of Patent: Sep. 17, 2019

(54) ILLUMINATION SYSTEM AND METROLOGY SYSTEM

(71) Applicant: ASML Netherlands B.V., Veldhoven (NL)

(72) Inventors: Johannes Matheus Marie De Wit, Helmond (NL); Kim Gerard Feijen, Overpelt (NL); Anko Jozef Cornelus Sijben, Veghel (NL); Martinus Maassen, Utrecht (NL); Henricus Martinus Johannes Van De Groes, Tiel (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/443,681

(22) Filed: Feb. 27, 2017

(65) Prior Publication Data
US 2017/0255105 A1    Sep. 7, 2017

(30) Foreign Application Priority Data
Mar. 7, 2016  (EP) .................................. 16158994

(51) Int. Cl.
*G03F 7/20* (2006.01)
*G01N 21/88* (2006.01)
(Continued)

(52) U.S. Cl.
CPC ..... *G03F 7/70191* (2013.01); *G01N 21/8806* (2013.01); *G02B 21/082* (2013.01);
(Continued)

(58) Field of Classification Search
CPC .... G03F 7/20; G03F 7/70191; G03F 7/70575; G03F 7/70616; G01N 21/88;
(Continued)

(56) References Cited

U.S. PATENT DOCUMENTS

| 5,784,152 A | 7/1998 | Heffelfinger et al. |
| 6,160,618 A | 12/2000 | Garner |

(Continued)

FOREIGN PATENT DOCUMENTS

| WO | WO 2009/078708 | 6/2009 |
| WO | WO 2009/106279 | 9/2009 |
| WO | WO 2015/143378 | 9/2015 |

OTHER PUBLICATIONS

International Search Report and Written Opinion of the International Searching Authority directed to International Application No. PCT/2017/053257, dated May 29, 2017; 15 pages.

(Continued)

*Primary Examiner* — Jamil Ahmed
(74) *Attorney, Agent, or Firm* — Sterne, Kessler, Goldstein & Fox P.L.L.C.

(57) ABSTRACT

Disclosed is an illumination system for a metrology apparatus and a metrology apparatus comprising such an illumination system. The illumination system comprises an illumination source; and a linear variable filter arrangement configured to filter a radiation beam from said illumination source and comprising one or more linear variable filters. The illumination system is operable to enable selective control of a wavelength characteristic of the radiation beam subsequent to it being filtered by the linear variable filter arrangement.

13 Claims, 6 Drawing Sheets

US 10,416,567 B2
Page 2

(51) Int. Cl.
*G02B 21/08* (2006.01)
*G02B 21/36* (2006.01)

(52) U.S. Cl.
CPC ......... *G02B 21/361* (2013.01); *G02B 21/365* (2013.01); *G03F 7/70575* (2013.01); *G03F 7/70616* (2013.01); *G01N 2021/8835* (2013.01)

(58) Field of Classification Search
CPC ........ G01N 21/8806; G01N 2021/8835; G01J 3/51; G01J 3/50; G06F 17/50; G06F 17/5068
See application file for complete search history.

(56) References Cited

U.S. PATENT DOCUMENTS

| | | | |
|---|---|---|---|
| 6,638,668 B2 | 10/2003 | Buchsbaum et al. | |
| 6,657,758 B1 | 12/2003 | Garner | |
| 6,700,690 B1 | 3/2004 | Buchsbaum et al. | |
| 7,015,484 B2 | 3/2006 | Gillispie et al. | |
| 7,030,978 B2 | 4/2006 | Guetta et al. | |
| 7,528,941 B2 | 5/2009 | Kandel et al. | |
| 7,619,735 B2 | 11/2009 | Milshtein | |
| 7,648,808 B2 | 1/2010 | Buchsbaum et al. | |
| 8,059,327 B1 | 11/2011 | Erdogan et al. | |
| 8,441,639 B2 | 5/2013 | Kandel et al. | |
| 8,681,413 B2 | 3/2014 | Manassen et al. | |
| 8,692,912 B2 | 4/2014 | Fish et al. | |
| 8,767,102 B2 | 7/2014 | Fish et al. | |
| 8,830,472 B2 | 9/2014 | Den Boef et al. | |
| 8,848,186 B2 | 9/2014 | Kandel et al. | |
| 8,873,054 B2 | 10/2014 | Kandel et al. | |
| 8,908,175 B1 | 12/2014 | Kandel et al. | |
| 9,080,971 B2 | 7/2015 | Kandel et al. | |
| 9,091,650 B2 | 7/2015 | Hill et al. | |
| 9,104,120 B2 | 8/2015 | Seligson et al. | |
| 9,116,103 B2 | 8/2015 | Wang et al. | |
| 9,341,769 B2 | 5/2016 | Manassen et al. | |
| 2007/0052961 A1 | 3/2007 | Lane et al. | |
| 2011/0027704 A1 | 2/2011 | Cramer et al. | |
| 2011/0043791 A1 | 2/2011 | Smilde et al. | |
| 2012/0242970 A1 | 9/2012 | Smilde et al. | |
| 2013/0100427 A1* | 4/2013 | Koolen | G03F 1/42 355/67 |
| 2013/0114085 A1 | 5/2013 | Wang et al. | |
| 2014/0104713 A1 | 4/2014 | Lane et al. | |
| 2014/0168650 A1 | 6/2014 | Manassen et al. | |
| 2014/0312212 A1* | 10/2014 | Schappacher | G01J 3/26 250/225 |
| 2015/0015874 A1 | 1/2015 | Chen et al. | |
| 2015/0022822 A1 | 1/2015 | Grunzweig et al. | |
| 2015/0186582 A1* | 7/2015 | Chen | G06F 17/5068 716/54 |
| 2015/0219449 A1 | 8/2015 | Bringoltz et al. | |
| 2016/0305766 A1 | 10/2016 | Manassen et al. | |

OTHER PUBLICATIONS

"VERIL Product Information", Advanced Optics, Schott AG (May 2013); 1 page. Available at http://www.schott.com/d/advanced_optics/ef0e4d95-b0d4-4e16-bc57-9c94c2536b13/1.0/schott-veril-may-2013-eng.pdf.

Anonymous, "Multiple rotatable color filter wheels for bandwidth optimization for CD and OVL determination in scatterometry", Questel Ireland Ltd., Research Disclosure, Database No. 533007 (2008); 4 pages.

Hodder et al., "New tunable filters for supercontinuum fiber lasers", Laser+Photonics 2014, Carl Hanser Verlag, Munich (2014), available at http://wvvw.deltaopticalthinfilm.com/wp-content/uploads/technical-notes/New%20tunable%20filters%20for%20Supercontinuum%20fiber%20lasers.pdf; 3 pages.

* cited by examiner

ILLUMINATION SYSTEM AND METROLOGY SYSTEM

BACKGROUND

Field of the Invention

The present invention relates to methods and apparatus of lithography usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

When performing such dark field scatterometry, different targets in different layers may show different behavior to different wavelength measurement radiation. Measurement radiation should therefore be individually tuned to a target and/or layer. Metrology apparatuses may be configured to allow wavelength selection from a few, typically around 7 to 10, discrete wavelengths evenly spread over the complete spectrum (which may range from 400 to 900 nm). Greater flexibility in wavelength selection is desirable.

SUMMARY OF THE INVENTION

The invention in a first aspect provides an illumination system for a metrology apparatus comprising: an illumination source; and a linear variable filter arrangement configured to filter a radiation beam from said illumination source and comprising one or more linear variable filters; wherein said illumination system is operable to enable selective control of a wavelength characteristic of the radiation beam subsequent to it being filtered by said linear variable filter arrangement.

The invention further provides for a metrology apparatus for measuring a parameter of a lithographic process, the metrology apparatus comprising the illumination system of the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENTS

Before describing embodiments of the invention in detail, it is instructive to present an example environment in which embodiments of the present invention may be implemented.

Figure 1:
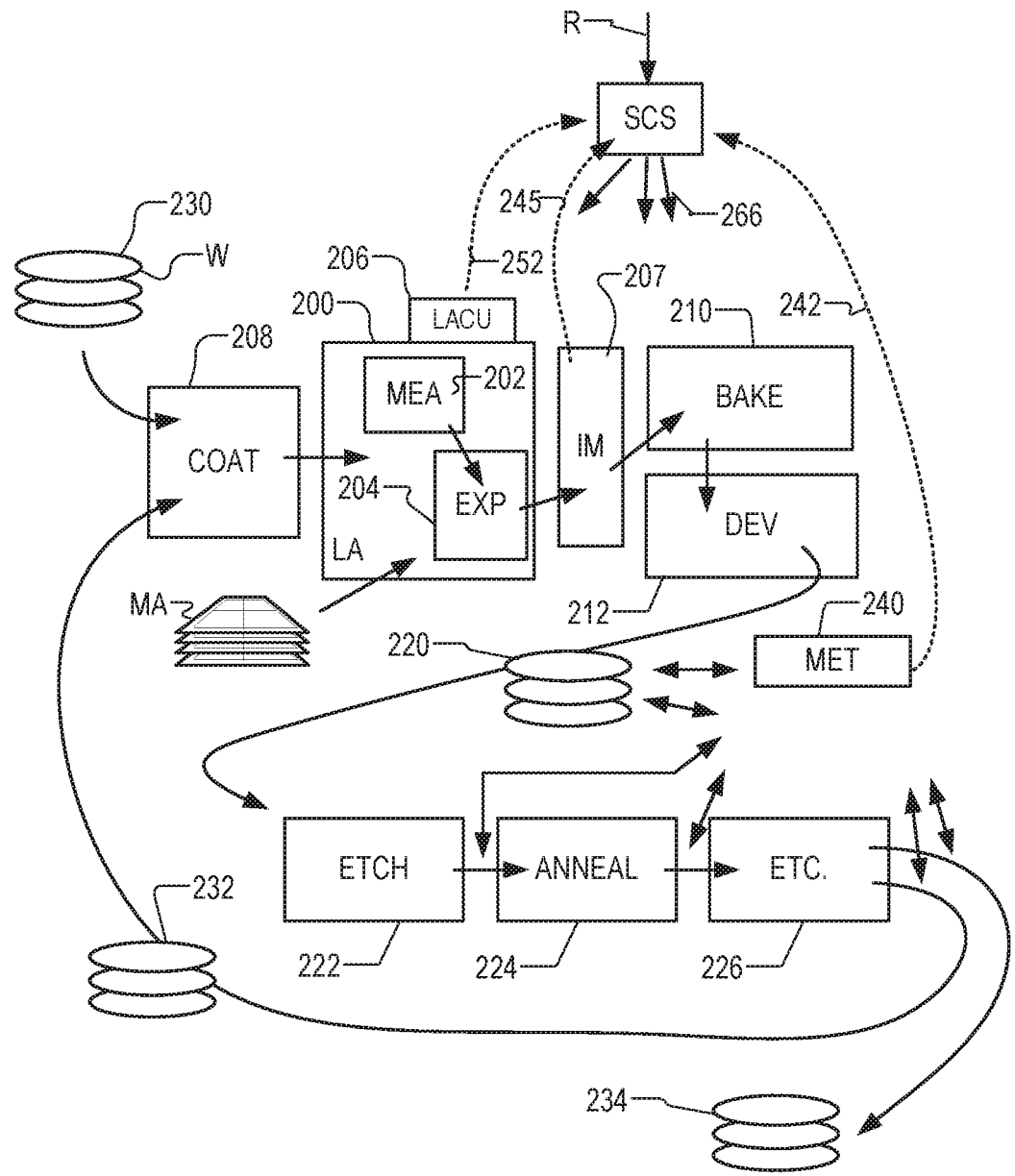
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located may also include one or more metrology systems. The metrology systems may include a stand-alone metrology apparatus MET 240 and/or an integrated metrology apparatus IM 207. The stand-alone metrology apparatus MET 240 receives some or all of the substrates W that have been processed in the litho cell for performing measurements offline. The integrated metrology apparatus IM 207 performs inline measurements and is integrated into the track to receive and measure some or all of the substrates W immediately after exposure. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed.

A common example of a metrology apparatus in a modern lithographic production facility is a scatterometer, for example an angle-resolved scatterometer or a spectroscopic scatterometer, and it may normally be applied to measure properties of the developed substrates at 220 prior to etching in the apparatus 222. Using stand-alone metrology apparatus 240 and/or integrated metrology apparatus 207, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

A metrology apparatus is shown in FIG. 2(a). The stand-alone metrology apparatus 240 and/or the integrated metrology apparatus 207 may comprise such a metrology apparatus, for example, or any other suitable metrology apparatus. A target T and diffracted rays of measurement radiation used to illuminate the target are illustrated in more detail in FIG. 2(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 2(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 2(a) and 2(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 2(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

Figure 2:
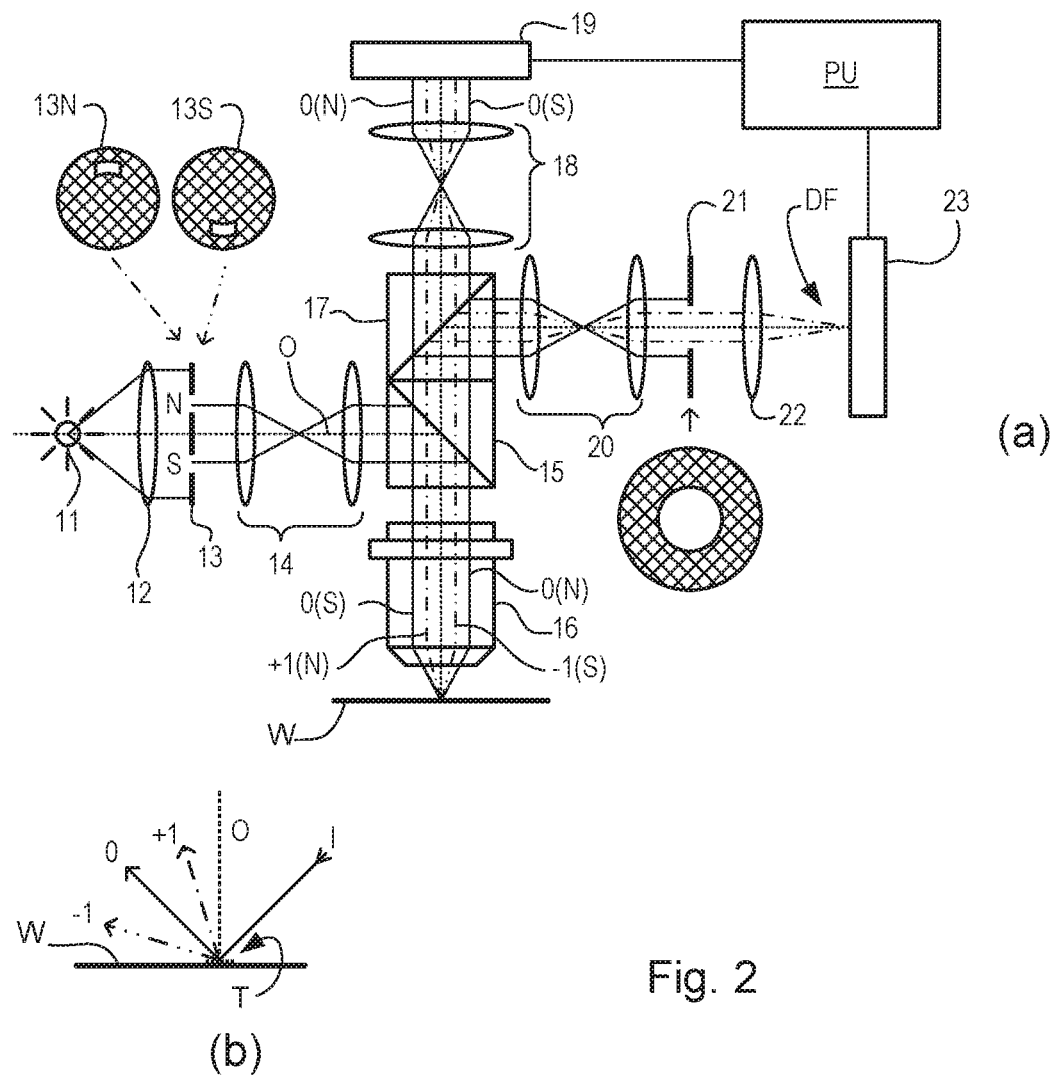
FIG. 2 comprises (a) a schematic diagram of a dark field scatterometer for use in measuring targets using a first pair of illumination apertures, (b) a detail of diffraction spectrum of a target grating for a given direction of illumination.

The particular forms of aperture plate 13 and field stop 21 shown in FIG. 2 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 2) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

Metrology apparatuses may allow selection of the wavelength of the measurement radiation. The measurement radiation from the source 11 may be filtered such that a specific measurement can be performed. The wavelength may be adjusted once per full substrate measurement. The optimal wavelength may be layer dependent. Typically, the metrology apparatus comprises a small number, possibly in the region of about 7 to 10, discrete filters to filter the measurement radiation, thereby enabling wavelength selection from only the same number of possible wavelengths. This can limit performance. Additionally, current switch time between discrete wavelengths is long and therefore can be adjusted only once per total substrate measurement.

Consequently, it is proposed to replace the discrete filters with one or more linear variable filters (LVFs). An LVF is a filter having spectral properties which vary substantially linearly with position in one (or more) direction along the filter. By moving the filter relative to a radiation beam (either by physically moving the filter, beam or both) such that the position which the beam passes through the filter is varied, the filtered beam wavelength may be varied linearly across a wide range of wavelengths (for example, between 400 nm and 900 nm). The output radiation beam may be a beam of measurement radiation for use in a metrology apparatus such as that illustrated in FIG. 2(*a*).

The simplest implementation of LVFs is a single tunable band pass filter where the output wavelength is selected simply by the spatial position on the filter. In embodiments, the LVF may comprise such a single tunable band pass filter. A more flexible filter can be designed however by combining two edge-pass LVFs, one long wave pass LVF and one short wave pass LVF, to create a tunable pass band. By moving both filters together, the central wavelength can be continuously adjusted and by moving the filters relative to one another the bandwidth of the combined filter can also be tuned. Consequently, in other embodiments, the LVF may comprise both a short wave pass filter and a long wave pass filter in series, thereby providing a band pass filter which can be tuned continuously across a large band of center wavelengths (e.g., between 400 nm and 900 nm), and/or different pass bands.

The use of an LVF addresses the issue of limited wavelength section choice. However, typical LVFs are heavy and large. Therefore switching of wavelengths during measurement of a single substrate is difficult. As such, in improved embodiments, a number of proposals enabling fast wavelength switching are proposed. By enabling wavelength selection that is relatively fast (e.g., possibly 50× faster than current arrangements with discrete filters or arrangements using present LVF designs) by using a low inertial mechanical design, multiple measurements with measurement radiation of different wavelengths can be performed on a single target. This provides the opportunity to optimize measurements for each target, and/or obtain increased measurement robustness (e.g., with respect to process variation) by using the results of different measurements. For example, better asymmetry correction can be obtained by combining measurements of multiple wavelengths (e.g. by using blind source separation techniques). The wavelength switch may be sufficiently fast such that multiple measurements can be performed on a single target in same time window as a single measurement is performed presently. This can improve accuracy (e.g., in measurement and/or reconstruction) and/or machine throughput e.g., by a factor of 2.

Figure 3:
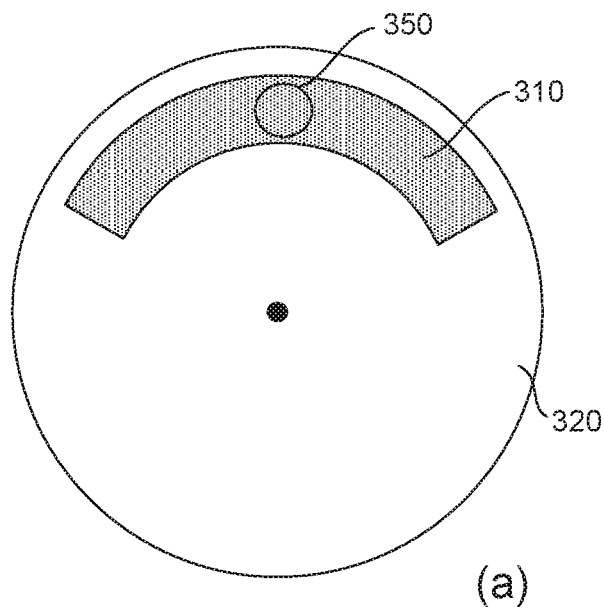
FIG. 3 shows (a)-(c) three alternative rotatably mounted filter element designs usable in embodiments of the invention.
Figure 3:
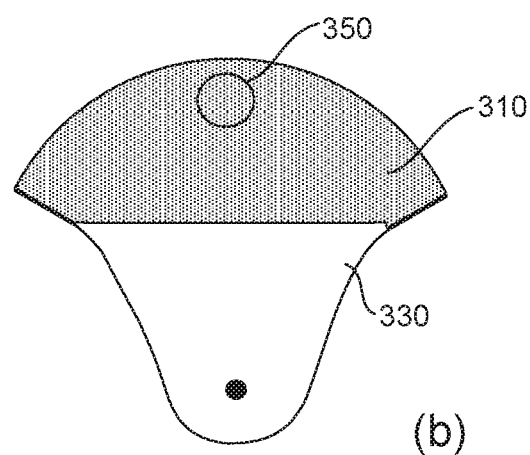
Figure 3:
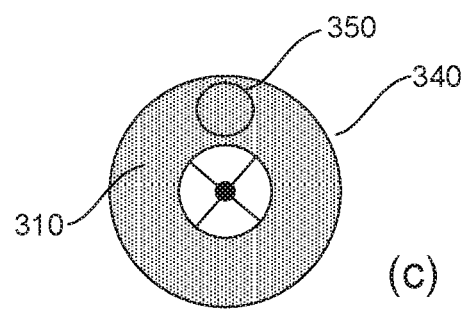

In one embodiment, the linear variable filter may be mounted onto a rotatably mounted filter element, such as a wheel or glass carrier. FIG. 3 shows three such embodiments. In FIG. 3(*a*), the LVF 310 is mounted to a wheel 320. In FIG. 3(*b*), the LVF 310 is coated onto a rotatably mounted transparent (e.g., glass) carrier 330. In FIG. 3(*c*) the LVF 310 is mounted or coated onto a small diameter wheel 340, such that it comprises or covers a large portion of the wheel 340. In this example, the LVF may be cut into pieces and applied to the wheel 340 in an overlapping manner. In each of these examples, the rotatably mounted filter element 320, 330, 340 is able to rotate such that the (e.g., fixed) radiation beam 350 is filtered by a different part of the LVF 310, depending on the angular position of the rotatably mounted filter element 320, 330, 340. Of course, these are only examples, and rotatably mounted filter elements comprising an LVF may take any number of different forms.

In any embodiment comprising a rotatably mounted filter element having an LVF, there may in fact be two such rotatably mounted filter elements in series: one being a short wavelength pass LVF and the other being a long wavelength pass LVF thereby providing a band pass filter. The two rotatably mounted filter elements preferably have individually controllable angular position such that the pass band and central wavelength is selectable. However, other embodiments are possible where the two rotatably mounted filter elements do not have individually controllable angular position, and therefore only the central wavelength is selectable.

Other embodiments may comprise scanning the radiation beam across the LVF. As before, the LVF may comprise a single band pass filter or pair of LVFs: a short wavelength pass LVF and long wavelength pass LVF in series. In the latter case, one, both or neither LVF may be moveable. As such, the main (fast) control of the central wavelength will be implemented by the scanning of the radiation beam across the LVF, while in embodiments where both LVFs are moveable, an additional optional control of the central wavelength may comprise moving the two LVFs together. Providing for relative movement of the two LVFs enables the pass band to be tunable by moving only one of the LVFs relative to the other. The beam may be made to scan across the LVF in numerous ways, including for example directing the beam using moveable optics, such as moveable (e.g., tilting) mirrors.

Figure 4:
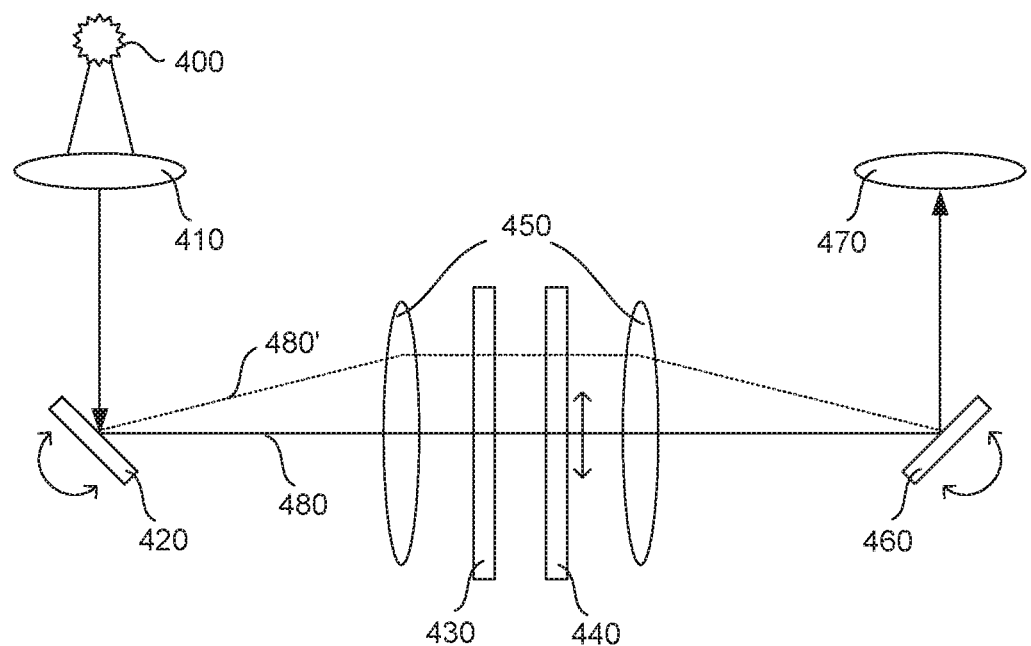
FIG. 4 shows an illumination system according to a first embodiment of the invention.

FIG. 4 shows such an arrangement having tilted mirrors. It comprises illumination source 400 (i.e., multiple wavelength source, for example, a white light or multiple wavelength source comprising a continuous spectrum of wavelengths), input lens 410, first tilting mirror 420, short wavelength pass LVF 430, long wavelength pass LVF 440, optical system 450, second tilting mirror 460 and output lens 470. Depending on the orientation of the tilting mirrors, the radiation beam passes through different sections of the short wavelength pass LVF 430 and long wavelength pass LVF 440. In the example shown, the beam is shown following a first path 480 and a second path 480', each path being the result of different positions of the tilting mirrors 420, 460. In this way the central wavelength of the filtered radiation can be quickly controlled. Of course the beam may be directed in other ways, including moveable (e.g., tiltably mounted) transmissive optics for example.

Figure 5:
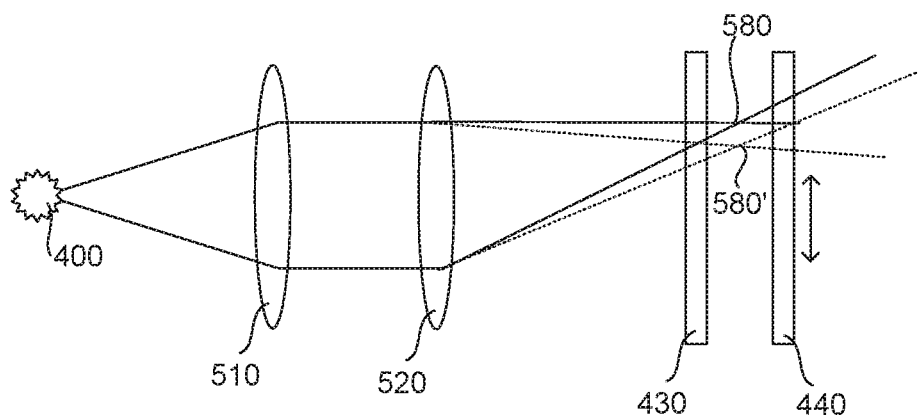
FIG. 5 shows an illumination system according to a second embodiment of the invention.

FIG. 5 shows an alternative beam scanning arrangement comprising an electroactive optic 520 (e.g., an electroactive lens comprising an electroactive liquid, such as nematic liquid crystal or electro-wetting principle) such that the output beam direction 580, 580' varies with the signal applied to it. Also shown are short wavelength pass LVF 430 and long wavelength pass LVF 440 and input lens 510, which operate as described in relation to FIG. 4.

In such scanning beam embodiments, one or both the short wavelength pass LVF 430 and long wavelength pass LVF 440 can be separately moveable to enable (albeit slower) control of the pass band. However, it is fast control of the central wavelength which is most relevant when performing multiple measurements of a substrate.

Other embodiments may comprise switching between two or more optical paths, each comprising at least one LVF, and preferably a pair of LVFs (comprising a short wavelength pass LVF and a long wavelength path LVF as described). One or both of the LVFs in one, some or all of the paths may be moveable to enable pass band selection and/or central wavelength selection in one, some or each path. Switching between paths allows very quick selection between two (or more depending on the number of paths) preselected pass bands and/or central wavelengths.

Figure 6:
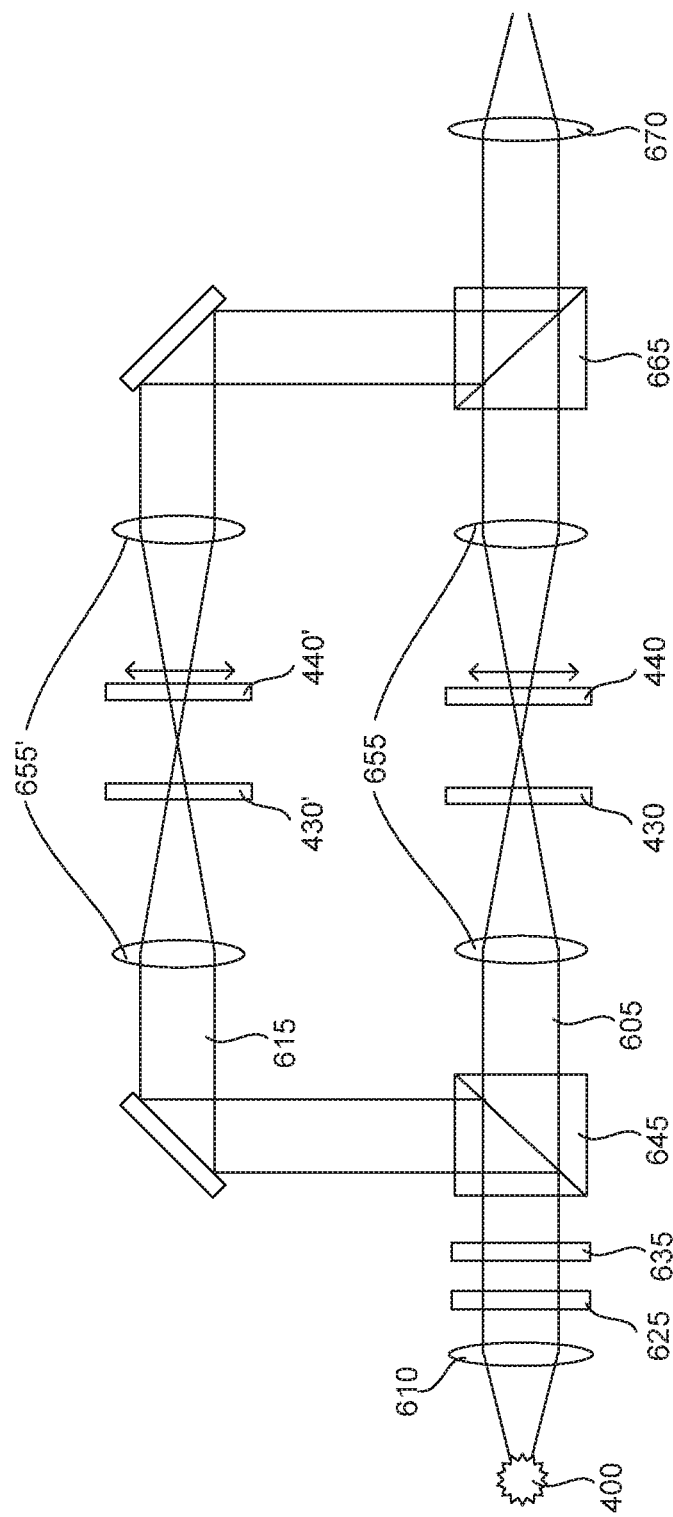
FIG. 6 shows an illumination system according to a third embodiment of the invention.

FIG. 6 shows a first path-switching embodiment comprising a first path 605 with a first pair of LVFs 430, 440 and a second path 615 comprising a second pair of LVFs 430', 440'. After input lens 610 there is a polarizer 625, variable retarder 635 (e.g., an electroactive optic such as one comprising (e.g., nematic) liquid crystal or a piezo elastic modulator) and a polarization sensitive beam splitter 645 in series. By control of the variable retarder 635, the beam polarization can be controlled, therefore enabling selectivity between first path 605 and second path 615. Also shown are focussing optics 655, 655' for each path, output beam splitter 665 and output lens 670.

Figure 7:
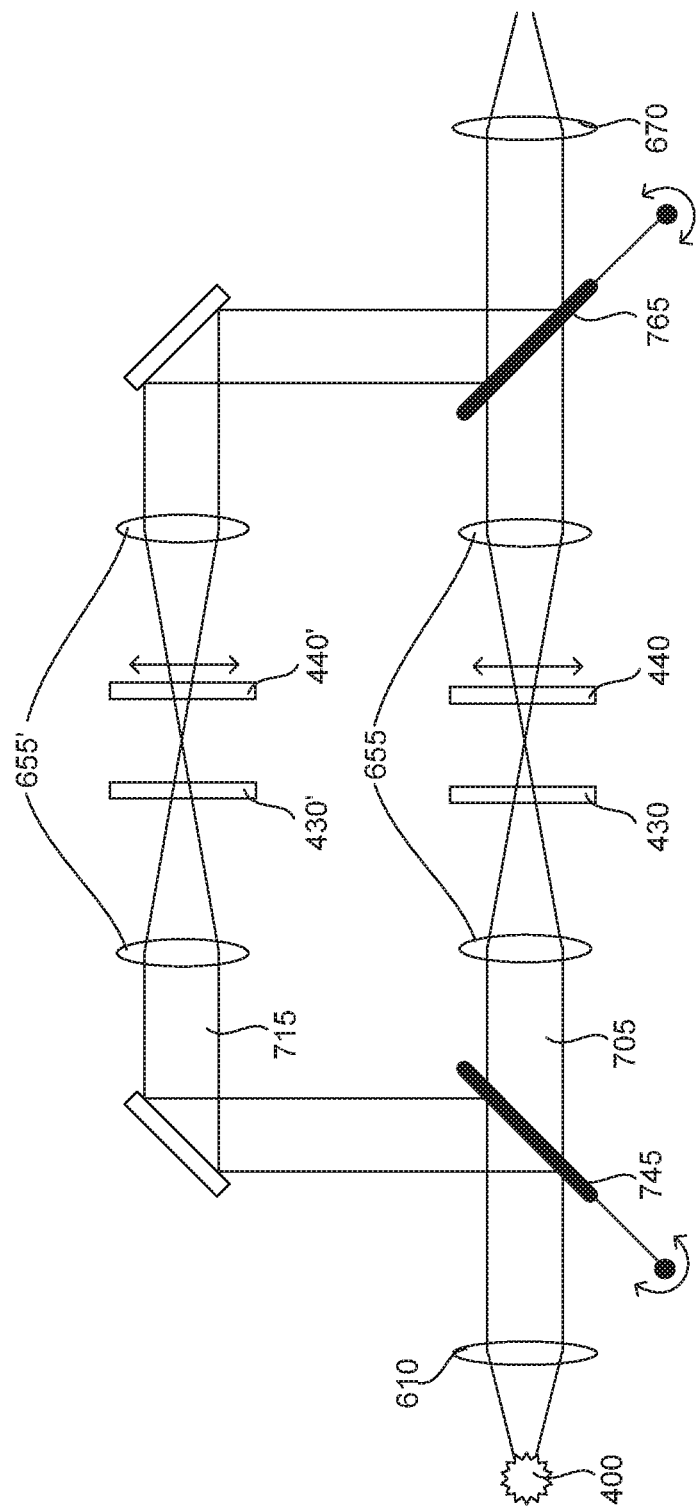
FIG. 7 shows an illumination system according to a fourth embodiment of the invention.

FIG. 7 shows a second path-switching embodiment. The basic principle is the same as that illustrated in FIG. 6. However, path switching is implemented by way of moveable optics 745, 765 (e.g. mirrors as shown here or lenses) which can be quickly switched in and out of the input beam path. In this way, the beam may be selectively diverted along second path 715, or not diverted such that it follows first path 705. Other arrangements can be readily envisaged, such as embodiments with more than two paths, or different arrangements for the movable optics.

The proposals described herein provide a continuously variable wavelength selection, where every central wavelength (and optionally pass band) can be simply adjusted. This provides the opportunity of optimizing for a specific layer (performance) or increased reconstruction accuracy (CD). Embodiments can provide a very fast switch time between different central wavelengths, with switching time in the region of 0.010 s, enabling throughput increase or single target accuracy improvement (reconstruction). Additionally, overlay, focus and CD measurements can be combined. Also, linear variable filters enable reduction or removal of the uniform color filters, saving money. The current wheels are large because of the large uniform filters and thus slow to move. The embodiments described herein enable compact design and faster move times.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system for measuring one or more characteristics of a target on a substrate formed by a lithographic process so that a parameter of the lithographic process can be determined, comprising:
    an illumination source configured to output a radiation beam;
    a linear variable filter arrangement, configured to filter the radiation beam from the illumination source, and comprising one or more linear variable filters;
    a support configured to support the substrate having the target formed thereon;
    beam directing optics configured to be selectively controlled to control a wavelength characteristic of the radiation beam subsequent to it being filtered by the linear variable filter arrangement to thereby direct the wavelength controlled radiation beam toward the target; and
    a scatterometry system configured to receive the wavelength controlled radiation beam interacting with the target,
    wherein the scatterometry system is configured to measure one or more of intensity and polarization of a portion of the received wavelength controlled radiation beam so the parameter of the lithographic process can be determined, and
    wherein the selective control comprises a control of the spatial position of the radiation beam on the one or more linear variable filters.

2. The system of claim 1, wherein:
    the linear variable filter arrangement comprises a pair of linear variable filters in series; and
    the pair of linear variable filters comprising a short wavelength pass linear variable filter and a long wavelength path linear variable filter which together provide a band pass linear variable filter.

3. The system of claim 2, wherein the short wavelength pass linear variable filter and the long wavelength path linear variable filter are configured for relative movement between the short wavelength pass linear variable filter and the long wavelength path linear variable filter enabling selection of a pass band of the band pass linear variable filter.

4. The system of claim 2, wherein the wavelength characteristic of the radiation beam comprises a central wavelength of a pass band of the band pass linear variable filter.

5. The system of claim 4, wherein the short wavelength pass linear variable filter and the long wavelength path linear variable filter are configured for movement together enabling selection of the central wavelength.

6. The system of claim 1, further comprising:
    one or more rotatably mounted filter elements;
    wherein each filter of the one or more linear variable filters is provided on one of the one or more rotatably mounted filter elements, and
    wherein the illumination system is operable such that the selective control of a wavelength characteristic is implemented by control of the angular position of the rotatably mounted filter elements.

7. The system of claim 1, wherein one or more linear variable filters of the linear variable filter arrangement is/are also selectively moveable relative to the radiation beam.

8. A system for measuring one or more characteristics of a target on a substrate formed by a lithographic process so that a parameter of the lithographic process can be determined, comprising:
    an illumination source configured to output a radiation beam;
    a linear variable filter arrangement, configured to filter the radiation beam from the illumination source, and comprising one or more linear variable filters;
    a support configured to support the substrate having the target formed thereon;
    beam directing optics configured to be selectively controlled to control a wavelength characteristic of the radiation beam subsequent to it being filtered by the linear variable filter arrangement to thereby direct the wavelength controlled radiation beam toward the target and
    a scatterometry system configured to receive the wavelength controlled radiation beam interacting with the target,
    wherein the scatterometry system is configured to measure one or more of intensity and polarization of a portion of the received wavelength controlled radiation beam so the parameter of the lithographic process can be determined, and
    wherein the selective control is implemented by providing for controllable relative movement between the radiation beam and the one or more linear variable filters.

9. A system for measuring one or more characteristics of a target on a substrate formed by a lithographic process so that a parameter of the lithographic process can be determined, comprising:
    an illumination source configured to output a radiation beam;
    a linear variable filter arrangement, configured to filter the radiation beam from the illumination source, and comprising one or more linear variable filters;
    a support configured to support the substrate having the target formed thereon;
    beam directing optics configured to be selectively controlled to control a wavelength characteristic of the radiation beam subsequent to it being filtered by the linear variable filter arrangement to thereby direct the wavelength controlled radiation beam toward the target; and
    a scatterometry system configured to receive the wavelength controlled radiation beam interacting with the target,
    wherein the scatterometry system is configured to measure one or more of intensity and polarization of a portion of the received wavelength controlled radiation beam so the parameter of the lithographic process can be determined, and
    wherein the beam directing optics are controllable to selectively direct the radiation beam to different spatial positions on the one or more linear variable filters of the linear variable filter arrangement.

10. The system of claim 9, wherein the beam directing optics comprise one or more tiltable mirrors.

11. The system of claim 9, wherein the beam directing optics comprise one or more electroactive optics.

12. The system of claim 11, further comprising a polarization sensitive beam splitter such that control of the one or more electroactive optics controls the polarization of the radiation beam and therefore the direction of the radiation beam out of the polarization sensitive beam splitter.

13. A system for measuring one or more characteristics of a target on a substrate formed by a lithographic process so that a parameter of the lithographic process can be determined, comprising:
   an illumination source configured to output a radiation beam;
   a linear variable filter arrangement, configured to filter the radiation beam from the illumination source, and comprising one or more linear variable filters;
   a support configured to support the substrate having the target formed thereon;
   beam directing optics configured to be selectively controlled to control a wavelength characteristic of the radiation beam subsequent to it being filtered by the linear variable filter arrangement to thereby direct the wavelength controlled radiation beam toward the target; and
   a scatterometry system configured to receive the wavelength controlled radiation beam interacting with the target,
   wherein the scatterometry system is configured to measure one or more of intensity and polarization of a portion of the received wavelength controlled radiation beam so the parameter of the lithographic process can be determined, and
   wherein the beam directing optics are controllable to selectively direct the radiation beam along alternative predetermined paths, each path comprising different ones of the linear variable filter arrangement.

* * * * *